(12) United States Patent
Yaegashi et al.

(10) Patent No.: US 6,840,735 B2
(45) Date of Patent: Jan. 11, 2005

(54) CENTRIFUGAL FLUID PUMP APPARATUS

(75) Inventors: Mitsutoshi Yaegashi, Nakai-machi (JP); Takehiko Asada, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 21 days.

(21) Appl. No.: 10/338,712

(22) Filed: Jan. 9, 2003

(65) Prior Publication Data

US 2003/0152462 A1 Aug. 14, 2003

(30) Foreign Application Priority Data

Jan. 9, 2002 (JP) ........................................ 2002-002584

(51) Int. Cl.[7] ............................. F04B 35/04; A61M 1/00
(52) U.S. Cl. .......................... 415/42; 417/44.11; 417/53; 417/423.12; 604/151
(58) Field of Search ........................... 417/42, 45, 44.1, 417/44.11, 420, 423.1, 423.7, 423.14, 356, 53, 423.12, 424.2; 415/206, 229; 604/6.11, 151

(56) References Cited

U.S. PATENT DOCUMENTS

| | | | |
|---|---|---|---|
| 5,725,357 A | * | 3/1998 | Nakazeki et al. ............. 417/18 |
| 5,947,703 A | * | 9/1999 | Nojiri et al. ................. 417/420 |
| 6,015,275 A | * | 1/2000 | Suzuki et al. ............ 417/423.12 |
| 6,071,093 A | | 6/2000 | Hart |
| 6,547,530 B2 | * | 4/2003 | Ozaki et al. ................. 417/44.1 |
| 6,626,644 B2 | * | 9/2003 | Ozaki .............................. 417/45 |

FOREIGN PATENT DOCUMENTS

| | | |
|---|---|---|
| EP | 1 027 898 A1 | 8/2000 |
| EP | 1 070 510 A2 | 1/2001 |

* cited by examiner

*Primary Examiner*—Charles G. Freay
(74) *Attorney, Agent, or Firm*—Burns, Doane, Swecker & Mathis, L.L.P.

(57) ABSTRACT

A centrifugal fluid pump apparatus includes a control mechanism; and a body 5 including a pump section having an impeller rotating inside a housing; a rotor having an impeller attraction magnet; a motor for rotating the rotor; an impeller attraction electromagnet for attracting the impeller thereto; an impeller-position detection sensor; and a groove for hydrodynamic bearing provided on an inner surface of the housing. The control mechanism has a position sensor output monitoring function or an electromagnet current monitoring function, a motor current monitoring function; and an emergency impeller rotation function. The impeller rotation function operates when the sensors or the electromagnet has a failure by using the position sensor output monitoring function or the electromagnet current monitoring function to rotate the impeller by utilizing the groove for hydrodynamic bearing.

20 Claims, 11 Drawing Sheets

CENTRIFUGAL FLUID PUMP APPARATUS

BACKGROUND OF THE PRESENT INVENTION

The present invention relates to a centrifugal fluid pump apparatus for pumping a medical fluid, typically blood.

In recent medical treatment, centrifugal blood pumps are increasingly used in artificial heart/lung units for extracorporeal blood circulation. Centrifugal pumps of the magnetic coupling type wherein a driving torque from an external motor is transmitted to an impeller through magnetic coupling are commonly used because the physical communication between the blood chamber of the pump and the exterior can be completely excluded and invasion of bacteria is prevented. The centrifugal blood pump includes a housing having a blood inlet port and a blood outlet port and an impeller rotatably accommodated in the housing to feed blood by a centrifugal force generated during its rotation. The impeller having a permanent magnet disposed therein is rotated by a rotor having magnets for attracting the magnet of the impeller thereto and by a rotational torque generation mechanism having a motor for rotating the rotor. The impeller rotates without contacting the housing, with the impeller being attracted to the side opposite to the rotor-disposed side by a magnetic force. This state is a magnetic levitation state.

In the case where a trouble occurs in the control system of the magnetic bearing of the conventional centrifugal pump, it is impossible to maintain the function of the centrifugal pump by rotating the impeller.

The centrifugal pump of a magnetic levitation type has three sensors for detecting the position of the impeller and three impeller attraction electromagnets. In the control of the magnetic bearing to be executed in the centrifugal pump, the position of the impeller is controlled by controlling electric current to be applied to the electromagnets, based on information of the impeller provided by the sensors for detecting the position of the impeller. Thus if devices constituting the control system are broken, for example, if cables for the position sensors and for the electromagnets are broken, the control system has troubles and a proper control cannot be accomplished. Thereby it is difficult to rotate the impeller by means of the magnetic bearing.

It is an object of the present invention to provide a centrifugal fluid pump apparatus allowing a rotation of an impeller without substantial contact between the impeller and an inner surface of a housing by utilizing a pressure generated by a groove for hydrodynamic bearing when a control system of a magnetic bearing has a trouble to thereby maintain feeding of a liquid, if the rotation of a motor can be controlled.

SUMMARY OF THE PRESENT INVENTION

The object described above is attained by the following a centrifugal fluid pump apparatus.

The centrifugal fluid pump apparatus comprises a pump body in which an impeller rotates without contacting a housing; and a control mechanism for said pump body, said pump body including: said housing having a blood inlet port and a blood outlet port; a centrifugal pump section including an impeller having a first magnetic material and a second magnetic material and rotating in said housing to feed a fluid by a centrifugal force generated during its rotation; an impeller rotational torque generation section including a rotor having a magnet for attracting said first magnetic material of said impeller and a motor for rotating said rotor; an impeller position control section having an electromagnet for attracting said second magnetic material of said impeller; a position sensor for detecting a position of said impeller; and a groove for hydrodynamic bearing provided on an inner surface of said housing at a side of said rotor or on a surface of said impeller at a side of said rotor, said control mechanism comprising: a position sensor output monitoring function or an electromagnet current monitoring function; a motor current monitoring function; a failure detection function for determining a failure of the sensor by using said position sensor output monitoring function or a failure of the electromagnet by using said electromagnet current monitoring function; and an emergency impeller rotation function operating when said failure detection function detects the failure of the sensor or the failure of the electromagnet to rotate said impeller by utilizing said groove for hydrodynamic bearing without substantial contact between said impeller and said housing, wherein said emergency impeller rotation function has: an impeller magnetic re-coupling execution function of stopping said electromagnet from attracting said impeller, when said failure detection function detects said failure and gradually decreasing a motor speed to thereby execute magnetic coupling between said impeller and said rotor; a magnetic re-coupling detection function of detecting magnetic re-coupling between said impeller and said rotor by using a motor current monitored by said motor current monitoring function; and a motor speed control function by increasing the motor speed up to a predetermined value after said magnetic re-coupling detection function detects said magnetic re-coupling.

BRIEF DESCRIPTION OF THE DRAWINGS

The above and other objects, features and advantages of the present invention will be better understood by reading the following description, taken in conjunction with the accompanying drawings.

DETAILED DESCRIPTION OF THE PREFERRED EMBODIMENTS

Figure 1:
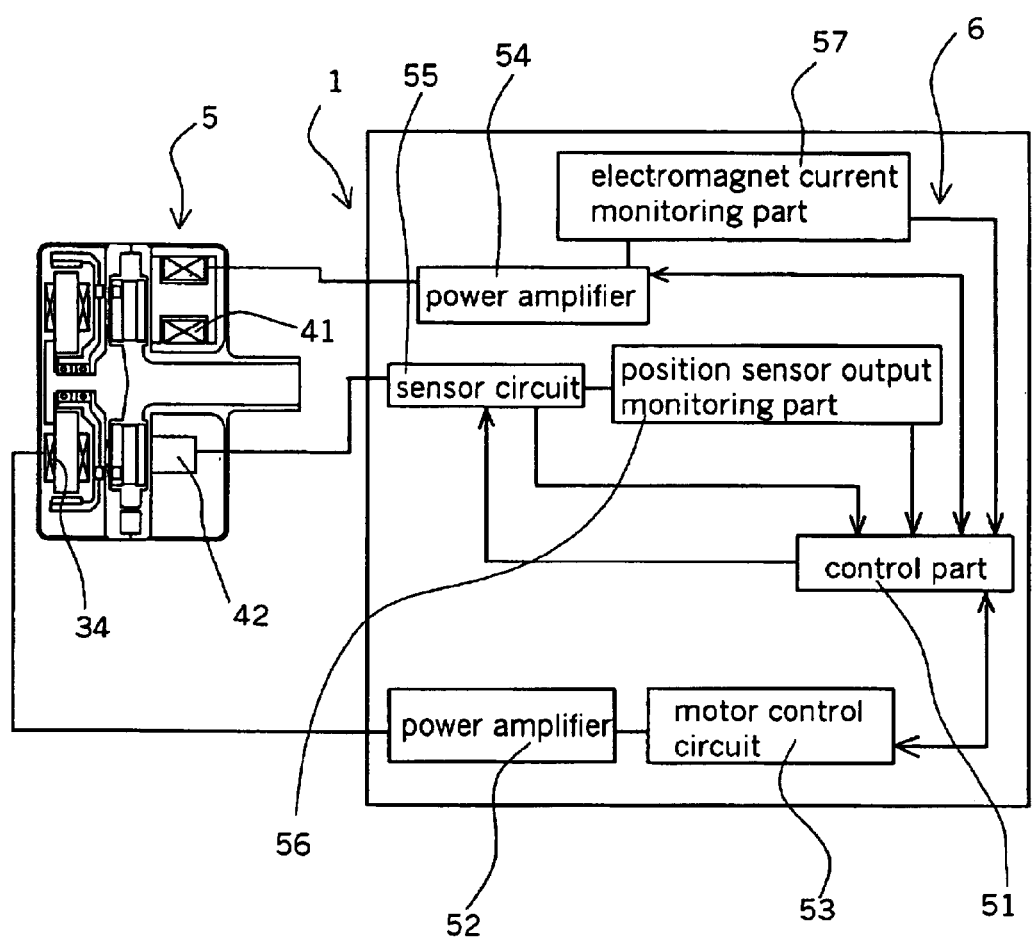
FIG. 1 is a block diagram showing a centrifugal fluid pump apparatus according to an embodiment of the present invention.
Figure 2:
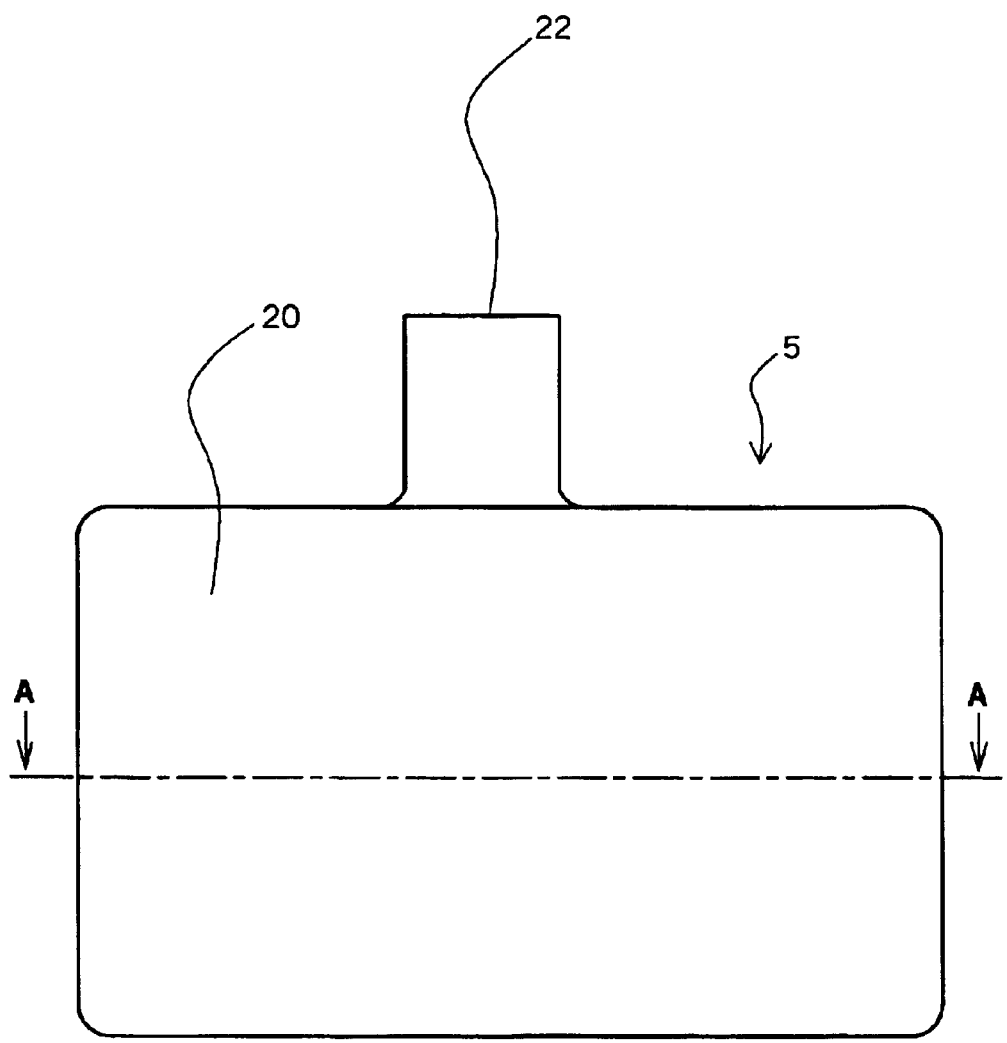
FIG. 2 is a front view showing an example of the body of the centrifugal fluid pump apparatus of the present invention.

An embodiment of the centrifugal fluid pump apparatus according to the present invention is described below with reference to drawings.

A centrifugal fluid pump apparatus 1 of the present invention includes a pump body 5 in which an impeller 21 rotates without contacting a housing 20; and a control mechanism 6 for the body 5.

The pump body 5 includes the housing 20 having a blood inlet port 22 and a blood outlet port 23; a centrifugal fluid pump section 2 including an impeller 21 having a first magnetic material 25 and a second magnetic material 28 disposed therein and rotating in the housing 20 to feed a fluid by a centrifugal force generated during its rotation; an impeller rotational torque generation section 3 including a rotor 31 having a magnet 33 for attracting thereto the first magnetic material 25 of the impeller 21 and a motor 34 for rotating the rotor 31; an impeller position control section 4 having an electromagnet 41 (electromagnet for attracting the second magnetic material 28 of the impeller 21 thereto) for attracting the impeller 21 thereto, a position sensor 42 (position sensor for detecting the position of the second magnetic material 28 of the impeller 21) for detecting the position of the impeller 21, and a groove 38 for hydrodynamic bearing provided on an inner surface of the housing 20 at the side of the rotor 31 or a surface of the impeller 21 at the side of the rotor 31.

The control mechanism 6 has a position sensor output monitoring part (position sensor output monitoring function) 56, a motor current monitoring function or an electromagnet current monitoring function 57, and a failure detection function. The failure detection function for determining a failure of the sensor 42 by using said position sensor output monitoring function or a failure of the electromagnet 41 by using said electromagnet current monitoring function.

As shown in FIG. 1, it is preferable that the control mechanism 6 has the position sensor output monitoring function 56, the electromagnet current monitoring function 57, the motor current monitoring function, and the failure detection function of determining whether the sensor has a failure by using the position sensor output monitoring function 56 and whether the electromagnet has a failure by using the electromagnet current monitoring function 57.

The centrifugal fluid pump apparatus 1 has an emergency impeller rotation function that operates when the failure detection function has detected that the sensor or the electromagnet has a failure to rotate the impeller 21 by utilizing the groove 38 for hydrodynamic bearing without substantial contact between the impeller 21 and the housing 20.

The emergency impeller rotation function includes an impeller magnetic re-coupling execution function of stopping the electromagnet 41 from attracting the impeller 21 when the failure detection function detects the failure and gradually decreasing (for example, successively or stepwise) a motor speed to thereby execute magnetic coupling between the impeller 21 and the rotor 31; a magnetic re-coupling detection function of detecting magnetic re-coupling between the impeller and the rotor by using a motor current monitored by the motor current monitoring function; and a motor speed control function by increasing the motor speed up to a predetermined value (for example, gradually, namely, successively or stepwise) after the magnetic re-coupling detection function detects that the magnetic re-coupling between the impeller and the rotor has been made.

That is, when the sensor or the electromagnet has a failure, the centrifugal fluid pump apparatus 1 of the present invention has the function of shifting from the non-contact rotation of the impeller by means of the magnetic bearing to the non-contact rotation of the impeller by means of the groove for hydrodynamic bearing that generates a pressure.

In the rotation of the impeller 21 made by means of the groove for hydrodynamic bearing, it is necessary to balance a magnetic attraction force acting between the impeller and the rotor with the pressure generated by the groove for hydrodynamic bearing in a direction opposite to the direction of the magnetic attraction force. To do so, the magnetic coupling between the impeller and the rotor is essential. Therefore in the case where the control system of the magnetic bearing has a trouble and thus the impeller and the rotor are magnetically uncoupled from each other, only machining of the groove for hydrodynamic bearing does not allow the shift from the rotation of the impeller by means of the magnetic bearing to the rotation thereof by means of the groove for hydrodynamic bearing.

Description will be made on an embodiment of the centrifugal fluid pump apparatus of a type having the position sensor output monitoring function 56 and the electromagnet current monitoring function 57 shown in FIG. 1 and capable of making determination as to whether the sensor and the electromagnet have a failure.

As shown in FIGS. 2 through 6, the body 5 has the housing 20 having the blood inlet port 22 and the blood outlet port 23, the centrifugal fluid pump section 2 having the impeller 21 rotating inside the housing 20 to feed blood by a centrifugal force generated during its rotation, the impeller rotational torque generation section (non-contact type magnetic bearing constructing section) 3 for the impeller 21, and the impeller position control section (contact type magnetic bearing constructing section) 4 for the impeller 21.

Figure 4:
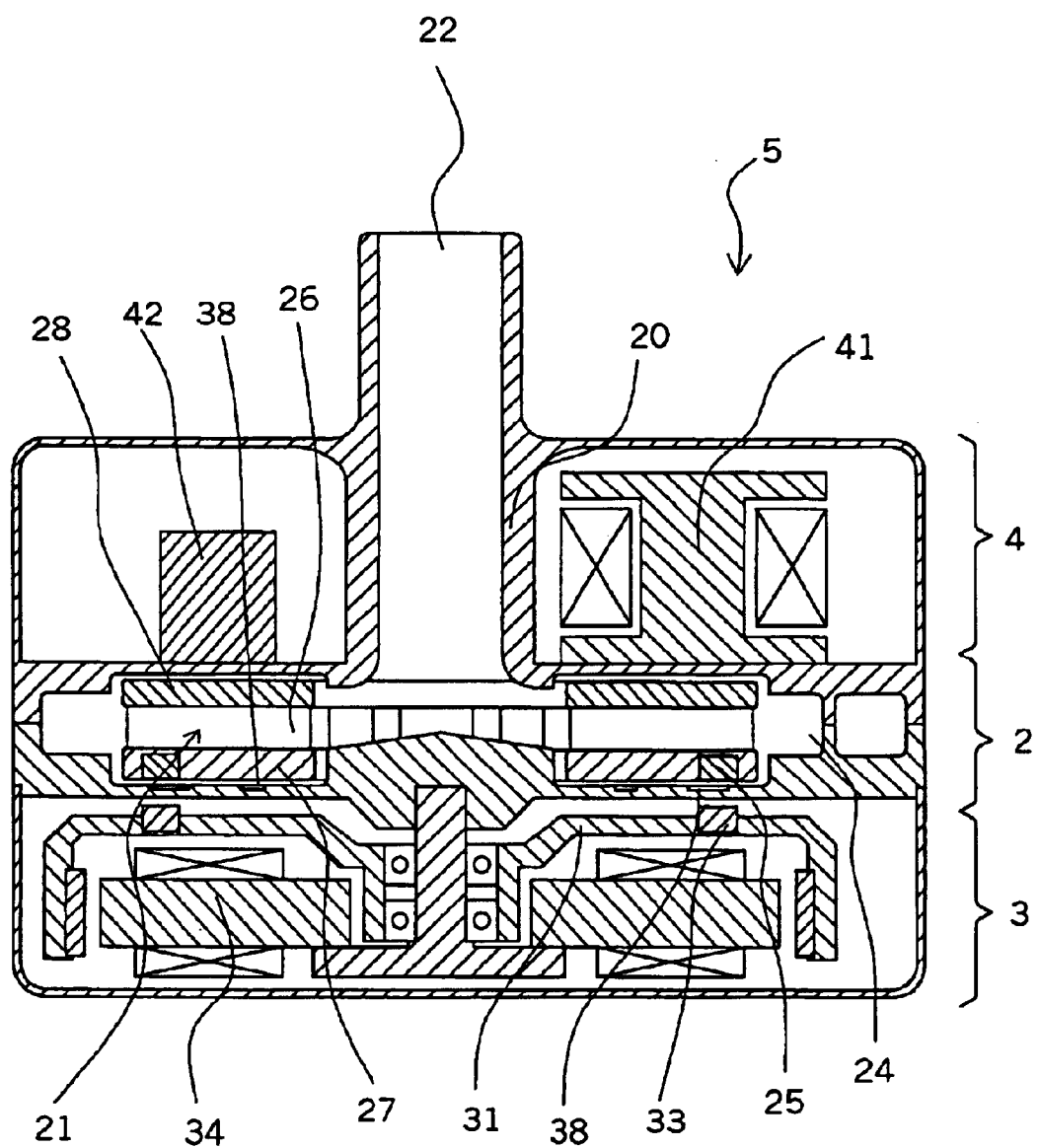
FIG. 4 is a vertical sectional view showing the body of the centrifugal fluid pump apparatus of the embodiment shown in FIG. 2.

As shown in FIG. 4, at a normal time, the impeller 21 rotates without contacting the inner surface of the housing 20, with the impeller 21 held at a predetermined position inside the housing 20 by the operation of the non-contact type magnetic bearing constructing section 3 and that of the contact type magnetic bearing constructing section 4.

Figure 3:
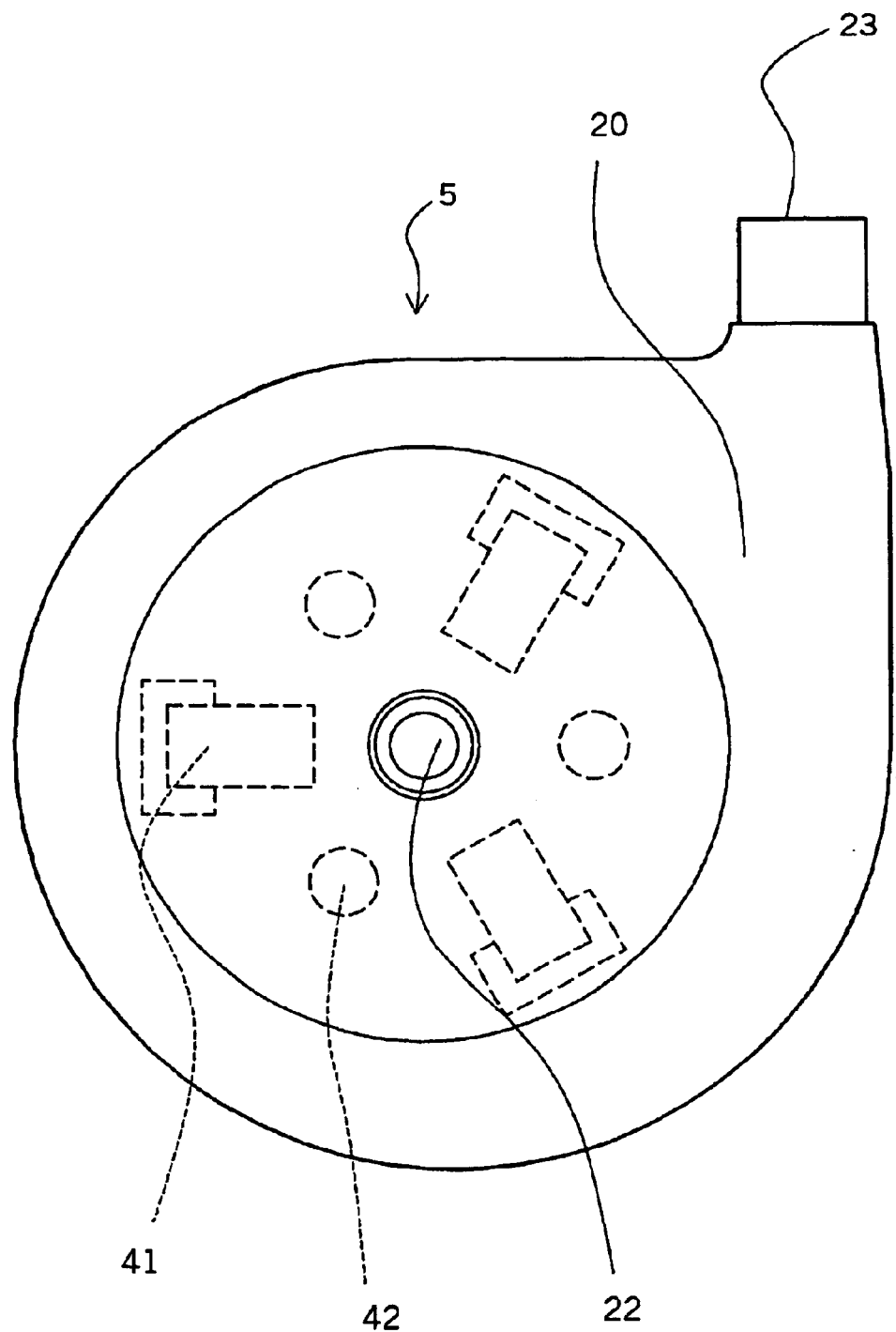
FIG. 3 is a plan view showing the body of the centrifugal fluid pump apparatus of the present invention shown in FIG. 2.
Figure 5:
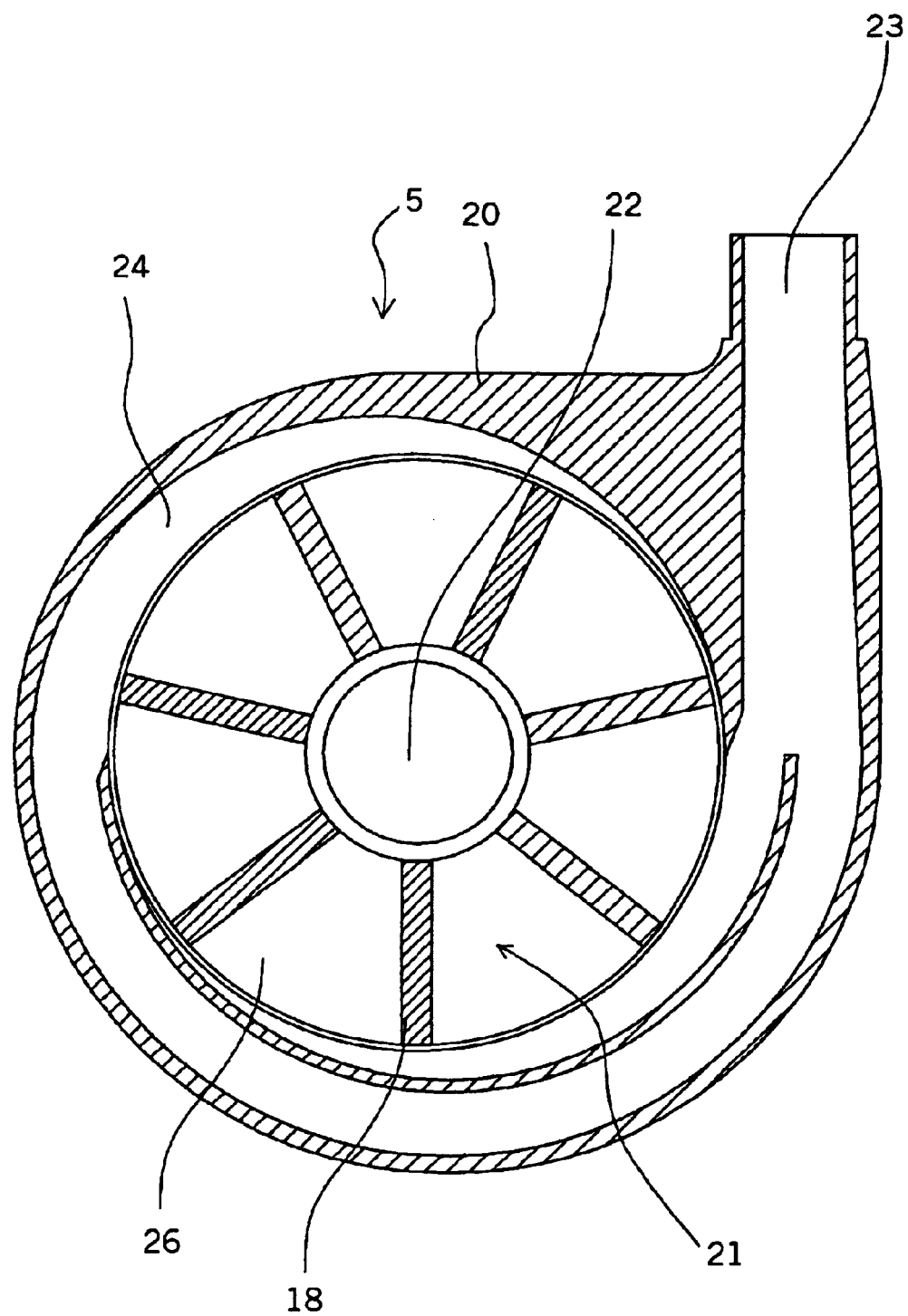
FIG. 5 is a sectional view taken along a line A—A in FIG. 2 showing the body of the centrifugal fluid pump apparatus.

The housing 20 has the blood inlet port 22 and the blood outlet port 23 and is formed of a non-magnetic material. The housing 20 accommodates a blood chamber 24 communicating with the blood inlet and outlet ports 22 and 23. The housing 20 also accommodates the impeller 21 therein. The blood inlet port 22 projects substantially vertically from the vicinity of the center of the upper surface of the housing 20. As shown in FIGS. 3 and 5, the blood outlet port 23 projects tangentially from a side surface of the approximately cylindrical housing 20.

As shown in FIG. 5, the disc-shaped impeller 21 having a through-hole in the center thereof is accommodated inside the blood chamber 24 formed inside the housing 20. As shown in FIG. 4, the impeller 21 includes an annular plate-shaped member (lower shroud) 27 forming the lower surface thereof, an annular plate-shaped member (upper shroud) 28 forming the upper surface thereof and opening at the center thereof, and a plurality of (for example, seven)

vanes 18 formed between the lower shroud 27 and the upper shroud 28. A plurality of (for example, seven) blood passages 26 partitioned from one another by the adjacent vanes 18 is formed between the lower shroud 27 and the upper shroud 28. As shown in FIG. 5, each of the blood passages 26 communicates with the center opening of the impeller 21 and extends from the center opening of the impeller 21 to its periphery, with each of the blood passages 26 becoming gradually larger in the width thereof. In other words, the vanes 18 are formed between the adjacent blood passages 26. In the embodiment, the vanes 18 and blood passages 26 are spaced at equiangular intervals and in substantially the same shape.

As shown in FIG. 4, a plurality (for example, 24) of the first magnetic materials 25 (for example permanent magnet, follower magnet) are embedded in the impeller 21. In the embodiment, the first magnetic materials 25 are embedded in the lower shroud 27. The embedded first magnetic materials 25 are provided so that the impeller 21 is attracted toward the side opposite to the side where the blood inlet port 22 (in other words, a side of the rotor 31) is disposed by a permanent magnet 33 provided in the rotor 31 of the rotational torque generation section 3 to be described later and that the rotational torque is transmitted from the rotational torque generation section 3 to the impeller 21.

The magnetic coupling, to be described later, between the impeller 21 and the rotor 31 is ensured by embedding a plurality of the first magnetic materials 25 in the impeller 21. It is preferable that each of the first magnetic materials 25 (permanent magnet) is circular in a horizontal cross section. Instead, it is possible to use a ring-shaped magnet having multi-poles (for example, 24 poles). In other words, a plurality of small magnets may be arranged in the shape of a ring in such a way that positive and negative poles alternate with each other.

The impeller 21 further includes the second magnetic member 28 which itself constitutes the upper shroud or which is provided inside the upper shroud. In the embodiment, the entire upper shroud is constructed of the second magnetic member 28. The second magnetic member 28 is provided so that the electromagnet 41 of the impeller position control section 4 to be described later attracts the impeller 21 magnetically toward the blood inlet port 22. The second magnetic member 28 is made of magnetic stainless steel.

The impeller position control section 4 and the rotational torque generation section 3 constitute a non-contact type magnetic bearing, which magnetically attracts the impeller 21 from opposite directions. Thereby the impeller 21 is held steadily at a proper position not in contact with the inner surface of the housing 20 and rotates inside the housing 20 without contacting its inner surface.

As shown in FIG. 4, included in the rotational torque generation section 3 are the rotor 31 accommodated in the housing 20 and a motor 34 for rotating the rotor 31. The rotor 31 has a plurality of permanent magnets 33 disposed on a surface thereof at the side of the centrifugal fluid pump section 2. The center of the rotor 31 is fixedly secured to the rotational shaft of the motor 34. A plurality of the permanent magnets 33 are equiangularly distributed in accordance with the arrangement mode (number and position) of the permanent magnets 25 of the impeller 21.

The impeller rotation torque generation section 3 is not limited to the illustrated one having the rotor and motor. For example, a plurality of stator coils may be used as the impeller rotation torque generation section 3 as long as they can attract the permanent magnets 25 of the impeller 21 thereto and drive the impeller 21 for rotation.

As shown in FIGS. 3 and 4, included in the impeller position control section 4 are a plurality of the electromagnets 41, accommodated in the housing 20, for attracting the second magnetic member 28 of the impeller 21 thereto and a plurality of position sensors 42 for detecting the positions of the second magnetic members 28 of the impeller 21. The electromagnets (three) 41 and the position sensors (three) 42 are spaced at equiangular intervals respectively. The electromagnets 41 and the sensors 42 are also spaced at equiangular intervals. Each of the electromagnets 41 consists essentially of a core and a coil. Three electromagnets 41 are arranged in the embodiment. Not less than three electromagnets, for example, four electromagnets may be provided. By adjusting the electromagnetic forces of the electromagnets 41 in accordance with results of detection of the position sensors 42, it is possible to balance forces acting on the impeller 21 in a rotational axis (z-axis) direction and control moments about an x-axis and a y-axis both perpendicular to the rotational axis (z-axis).

Each of the position sensors 42 detects the distance of the gap between the electromagnet 41 and the second magnetic member 28. An output of the position sensor 42 indicating the result of the detection is sent to a control part 51 of the control mechanism 6 for controlling electric current to be applied to the coil of the electromagnet (hereinafter referred to as electromagnet current) or a voltage to be applied thereto. When a radial force such as gravity acts on the impeller 21, the impeller 21 is held at the center of the housing 20 by virtue of restoring forces of a magnetic flux between the permanent magnet 25 of the impeller 21 and the permanent magnet 33 of the rotor 31 and restoring forces of a magnetic flux between the electromagnet 41 and the second magnetic member 28.

Figure 6:
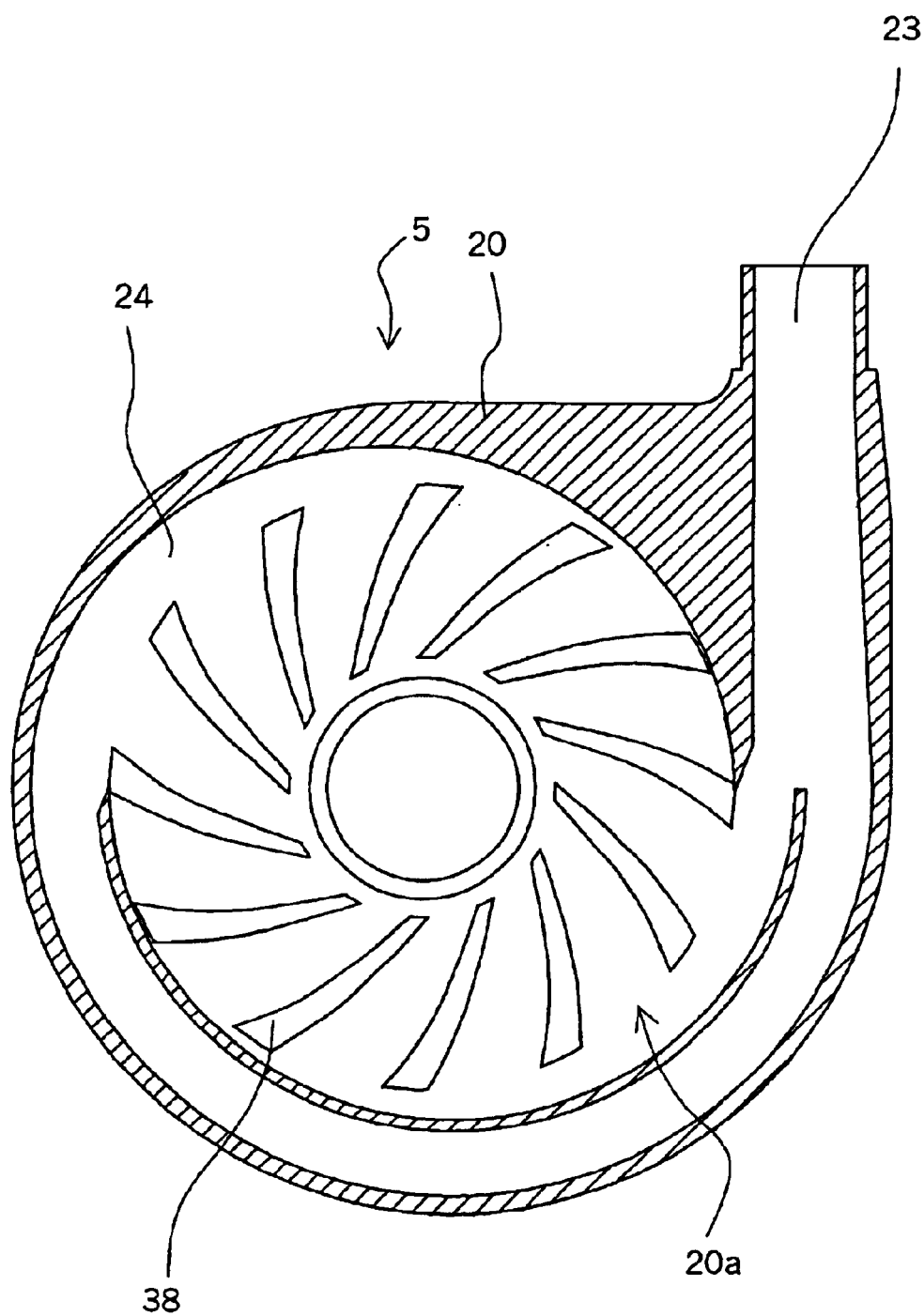
FIG. 6 is a sectional view showing a state in which an impeller has been removed from the sectional view taken along the line A—A in FIG. 2 showing the body of the centrifugal fluid pump apparatus.

As shown in FIG. 6, in the pump body 5 of the embodiment, the housing 20 accommodates the impeller 21 and has the groove 38 for hydrodynamic bearing formed on an inner surface 20a of the housing 20 at the rotor-disposed side, the inner surface 20a of whose forms the blood chamber 24. When the operation of the magnetic bearing stops (in other words, when the operation of the electromagnetic stops), a hydrodynamic bearing effect generated between the groove 38 for hydrodynamic bearing and the impeller 21 by rotation of the impeller 21 at a speed more than a predetermined one allows the impeller 21 to rotate without contacting the inner surface of the housing 20.

As shown in FIG. 6, the groove 38 for hydrodynamic bearing has a size corresponding to that of the bottom surface of the impeller 21 (the surface of a rotor side). In the centrifugal fluid pump apparatus 1 of the embodiment, the groove 38 for hydrodynamic bearing extends spirally (in other words, curved) outwardly to the vicinity of the outer edge of the inner surface 20a, with one end of the groove 38 for hydrodynamic bearing disposed on the circumference of a circle spaced outward at a short distance from the center of the inner surface 20a of the housing 20 and with the width thereof becoming outwardly gradually larger. A plurality of the grooves 38 for hydrodynamic bearing has substantially the same configuration and is spaced at almost equal intervals. Each of the groove 38 for hydrodynamic bearing is concavely formed. It is preferable that the depth thereof is in the range of 0.01 to 0.2 mm. It is also preferable that the number of the groove 38 for hydrodynamic bearing is in the range of 6 to 36. In the embodiment, 12 grooves 38 for hydrodynamic bearing 38 are provided at equiangular intervals around the center of the axis of the impeller 21.

The groove 38 for hydrodynamic bearing may be disposed on the surface of the impeller 21 at the side of the rotor 31 instead of disposing it on the housing 20. It is preferable that the groove 38 for hydrodynamic bearing disposed on the surface of the impeller 21 at the side of the rotor 31 has the same construction as that of the groove 38 for hydrodynamic bearing disposed on the inner surface of the housing 20.

The groove 38 for hydrodynamic bearing having the above-described construction is attracted toward the impeller torque generation section 3, when the impeller position control section 4 does not operate. Owing to the hydrodynamic bearing effect generated between the groove 38 for hydrodynamic bearing and the bottom surface of the impeller 21 (or between the groove 38 for hydrodynamic bearing and the inner surface of the housing), the impeller 21 rotates at a position spaced at a short distance from the inner surface of the housing 20 without contacting the inner surface thereof, thus providing a blood passage between the lower surface of the impeller 21 and the inner surface of the housing 20. Thereby it is possible to prevent blood from staying therebetween and thrombus from occurring owing to the stay of the blood therebetween. In addition, the groove 38 for hydrodynamic bearing displays an agitating action between the lower surface of the impeller 21 and the inner surface of the housing 20 in a normal state, thus preventing the blood from partially staying therebetween.

The control mechanism 6 will be described below with reference to FIG. 1.

The control mechanism 6 includes a power amplifier 52 for the magnetic coupling motor 34, a motor control circuit 53, a power amplifier 54 for the electromagnet 41, the electromagnet current monitoring part 57 for monitoring electric current to be applied to the electromagnet 41, a sensor circuit 55 for the sensor 42, the position sensor output monitoring part 56 for monitoring the output of the sensor 42, and the control part 51. The control part 51 has the motor current monitoring function.

In the embodiment, the control mechanism 6 has both the electromagnet current monitoring part 57 and the position sensor output monitoring part 56. But the control mechanism 6 may have the electromagnet current monitoring part 57 or the position sensor output monitoring part 56.

The centrifugal fluid pump apparatus 1 has the emergency impeller rotation function that operates when the failure detection function detects that the sensor or the electromagnet has a failure and allows the impeller 21 to rotate without contacting the housing 20 by utilizing the groove 38 for hydrodynamic bearing.

The control part 51 has the failure detection function of determining whether the sensor has a failure by using an output of the electromagnet current monitoring part or that of the sensor output monitoring part; the impeller re-coupling execution function of stopping the electromagnet 41 from attracting the impeller 21 thereto and gradually decreasing (for example, successively or stepwise) the motor speed when the failure detection function detects the failure to thereby execute the magnetic coupling between the impeller 21 and the rotor 31; the magnetic re-coupling detection function of detecting the magnetic re-coupling of the impeller to the rotor 31 by using a motor current monitored by the motor current monitoring function; and the motor speed control function by increasing the motor speed up to a predetermined value gradually (for example, successively or stepwise) after the magnetic re-coupling detection function detects the magnetic re-coupling of the impeller to the rotor.

The control mechanism 6 of the centrifugal pump of the embodiment has the position sensor output monitoring function and the electromagnet current monitoring function. When the control mechanism 6 detects that an output of the position sensor (plural systems are provided) or electromagnet current (plural systems are provided) deviates from a normal range, which causes control of the magnetic bearing cannot be performed owing to the magnetic uncoupling between the impeller and the rotor, the control mechanism 6 stops the electromagnet 41 from attracting the impeller 21 thereto and changes the motor speed to perform the magnetic re-coupling between the impeller and the rotor. Then the control mechanism 6 returns the motor speed to its original one after the control mechanism 6 detects that the magnetic re-coupling therebetween has been achieved to thereby shift the non-contact rotation of the impeller by means of the magnetic bearing to the non-contact rotation thereof by means of the groove 38 for hydrodynamic bearing.

If the sensor system of the magnetic bearing has a trouble owing to breakage of devices or disconnection of cables, the output of the sensor deviates from its normal range. For example, if a reluctance sensor has disconnection, the output thereof deviates from its normal range.

Thus the centrifugal fluid pump apparatus of the embodiment has a sensor circuit having a function of generating a predetermined output value exceeding the normal level when the sensor system has disconnection. More specifically, in the case where the normal range of the output of the sensor circuit is in the range of −1 to +1 [V] as the output of the sensor, the output of the sensor circuit is +2.5 [V] (predetermined value) when the sensor system has disconnection. Therefore the failure detection function is capable of determining easily and securely that the sensor has a failure (disconnection), when an output value of the sensor monitored by the sensor output monitoring function is equal to the predetermined output value at the time when the sensor system has disconnection.

Similarly to the sensor system, if the electromagnet current system has a trouble owing to breakage of devices or disconnection of cables, electric current to be applied to the electromagnet current system deviates from its normal range. Therefore the centrifugal fluid pump apparatus of the embodiment has a circuit for the electromagnet. The electromagnet circuit used in the embodiment is of a type not energized when the electromagnet has disconnection. More specifically, the normal range of electric current to be applied to the electromagnet circuit is in the range of 1 to 2 [A]. When the electromagnet circuit has disconnection, electric current of 0 [A] is applied thereto. Accordingly, the failure detection function is capable of determining easily and securely that the electromagnet has a failure (disconnection), when the electromagnet current monitoring function monitors that electric current is not applied to the electromagnet circuit.

The centrifugal fluid pump apparatus of the embodiment has a plurality of electromagnets. The electromagnet monitoring function monitors the output of each of the electromagnets. If any one of the electromagnets has a failure, the failure detection function determines that the electromagnet has a failure. Similarly, the centrifugal fluid pump apparatus of the embodiment has a plurality of position sensors. The sensor output monitoring function monitors the output of each of the position sensors. If any one of the position sensors, the failure detection function determines that the position sensor has a failure.

The dynamic pressure bearing constructed of the groove for hydrodynamic bearing is a system of maintaining the non-contact between the impeller 21 and the housing 20 by virtue of the pressure generated by the groove for hydrodynamic bearing. To generate the pressure, the impeller 21 is required to rotate at more than a certain speed. To do so, the magnetic coupling between the impeller and the rotor should be normal. If a failure has occurred in the control system of the magnetic bearing, the magnetic coupling between the impeller and the rotor becomes abnormal. Thus it is necessary to magnetically re-couple the impeller and the rotor to each other. In the centrifugal fluid pump apparatus of the present invention, the impeller is capable of accomplishing a stable non-contact rotation by means of the groove for hydrodynamic bearing, when the impeller speed (the rotor speed) is in the range of 1000 to 3000 rpm.

The impeller re-coupling execution function that operates after a failure is detected will be described below.

In the centrifugal fluid pump apparatus of the present invention, when the failure detection function detects a failure, the attraction of the impeller 21 to the electromagnet 41 is stopped. Consequently the impeller 21 is attracted toward the rotor 31 and approaches the inner surface of the housing 20. Then the magnetic coupling between the rotor 31 and the impeller 21 is executed in the state in which the magnetic coupling between the magnet of the rotor 31 and the magnetic material of the impeller 21 is easily achievable by decreasing the motor speed gradually (for example, namely, successively or stepwise).

It is preferable that the impeller re-coupling execution function has a first speed decrease step of successively decreasing the motor speed to a predetermined speed at a first decrease ratio; and a second speed decrease step of successively decreasing the motor speed at a second decrease ratio lower than the first decrease ratio, if the magnetic re-coupling of the impeller to the rotor is not detected at the first speed decrease step.

By using a motor current monitored by the motor current monitoring function, the impeller magnetic re-coupling detection function detects that the magnetic re-coupling between the impeller 21 and the rotor 31 has been accomplished. More specifically, when the magnetic re-coupling between the impeller 21 and the rotor 31 is achieved, the load to the motor increases. Consequently the motor current rises, which allows the detection of the magnetic re-coupling therebetween. More specifically, the re-coupling detection function determines that the magnetic re-coupling therebetween has been made, when a motor current value at a predetermined motor speed is more than a predetermined motor current value. In this case, the control part 51 stores the predetermined motor current value at the predetermined motor speed. In this manner, the control part 51 determines that the magnetic re-coupling therebetween has been accomplished. The control part 51 may store a predetermined motor current value for each of a plurality of predetermined motor speed. Thereby the control part 51 can determine that the magnetic re-coupling therebetween has been made, when a motor current value at each of the predetermined motor speed is more than the stored predetermined motor current value at each of the predetermined motor speed. It is preferable that the control part 51 stores a relation expression between the motor speed and the motor current value and the control part 51 can determine that the magic re-coupling has been made when the relation expression is satisfied.

The centrifugal fluid pump apparatus of the present invention has the motor speed control function. This function operates after the magnetic re-coupling between the impeller 21 and the rotor 31 is detected. This function increases the motor speed up to a predetermined one (at least the motor speed at which substantial non-contact rotation of the impeller by means of groove for hydrodynamic bearing is allowed). It is preferable that the centrifugal fluid pump apparatus (in other words, the control mechanism) has a motor speed storing function at the time when the failure detection function detects a failure or at a time in the neighborhood of the time when the failure detection function detects the failure. It is also preferable that the motor speed control function increases the motor speed to the one stored by the motor speed storing function.

It is also preferable that when the failure detection function detects that the sensor 42 or the electromagnet 41 has a failure, the emergency impeller rotation function of the centrifugal fluid pump apparatus allows the rotor 31 to rotate, with the impeller 21 in contact with the surface of the housing 20 opposite to the rotor-disposed side by attracting the impeller 21 to the electromagnet 41 to a higher extent at an arbitrary time. This function releases the state in which the impeller 21 is in contact with the inner surface of the housing at the rotor side and allows the shift preferably to the rotation of the impeller 21 that is made by utilizing the groove for hydrodynamic bearing.

It is also preferable that the centrifugal fluid pump apparatus (in other words, the control mechanism) has an uncoupling determination function that operates while the motor is rotating, with the motor speed being controlled by the motor speed control function, when the impeller is levitated by means of the dynamic pressure bearing after magnetic re-coupling of the impeller to the rotor is accomplished. The uncoupling determination function is capable of determining that the impeller and the rotor have been magnetically uncoupled from each other, when the motor speed is larger than a predetermined value during a predetermined time period and the motor current value is smaller than the predetermined motor current value. More specifically, the uncoupling determination function stores a predetermined motor current value (for example, 0.12 A) at a predetermined motor speed (for example, 1000 rpm). When an actual motor speed is larger than the predetermined motor speed and an actual motor current value is smaller than the stored predetermined motor current value, the uncoupling determination function determines that the impeller and the rotor have been magnetically uncoupled from each other.

It is also preferable that the centrifugal fluid pump apparatus has the function of stopping the rotation of the motor when the uncoupling determination function detects that the impeller and the rotor are uncoupled from each other.

It is also preferable that the centrifugal fluid pump apparatus has a second emergency impeller rotation function that operates in the case where the magnetic re-coupling of the impeller to the rotor is not accomplished by an impeller re-coupling execution function or when the impeller and the rotor are uncoupled from each other after they are re-coupled from each other.

The second emergency impeller rotation function includes a second impeller re-coupling execution function of rotating the rotor 31, with the impeller 21 in contact with the surface of the housing 20 opposite to the rotor-disposed side by attracting the impeller 21 to the electromagnet 41 to a higher extent, stopping the electromagnet 41 from attracting the impeller 21 thereto, and decreasing the motor speed gradually (successively or stepwise) to thereby execute the magnetic coupling between the impeller 21 and the rotor 31. In addition, the second emergency impeller rotation function includes the motor speed control function by increasing the motor speed up to a predetermined value (preferably gradually) after the magnetic re-coupling detection function detects that the magnetic re-coupling between the impeller 21 and the rotor 31 has been accomplished. It is preferable that the second impeller re-coupling execution function is the same as the impeller re-coupling execution function previously described. It is also preferable that the motor speed control function is the same as the one previously described.

Figure 7:
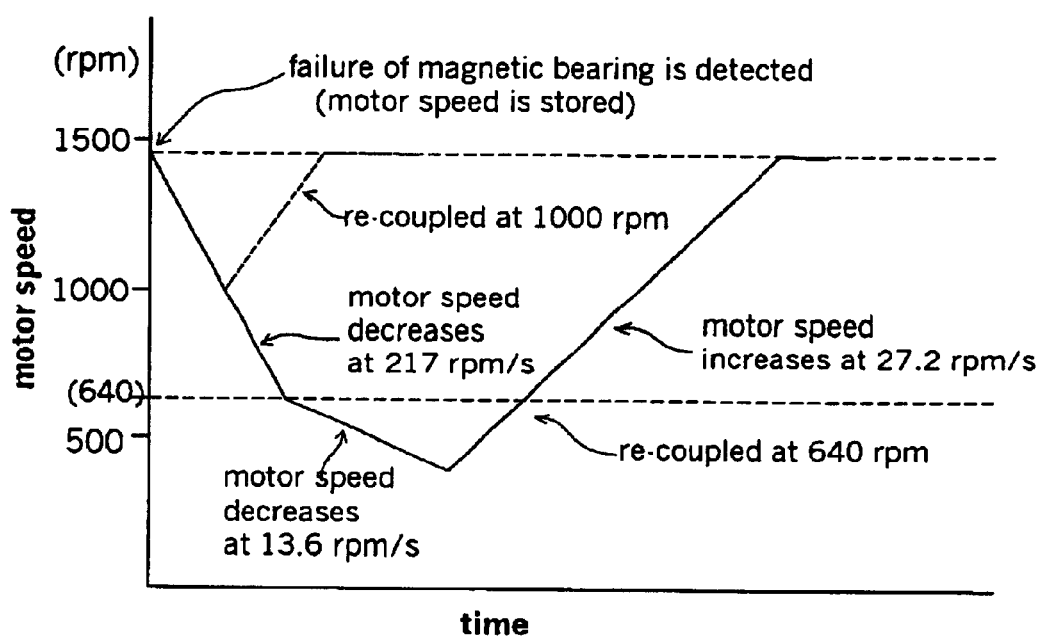
FIG. 7 is a timing chart for describing the operation of the centrifugal fluid pump apparatus of an embodiment of the present invention.

The operation of the centrifugal fluid pump apparatus of the present invention will be described below with reference to the timing chart shown in FIG. 7 and the flowcharts shown in FIGS. 8 and 9.

A magnetic bearing pump rotates at not less than 1200 rpm, more specifically, at 1450 rpm. If the control system of the magnetic bearing has a trouble (failure of magnetic bearing), as shown in the flowchart of FIG. 8, i.e., if the control part 51 determines that the sensor or the electromagnet has disconnection, an emergency rotation control mode starts to operate. The control part 51 stores the motor speed at the time when it is determined that the sensor or the electromagnet has disconnection.

Then the operation of the electromagnet is stopped to suspend the operation of the magnetic bearing. The motor speed is decreased at a predetermined decrease ratio (first decrease ratio: in the range of 50 to 400 rpm/s, 217 rpm/s in the embodiment). This state is an impeller magnetic re-coupling execution step.

If a motor current value is not less than the predetermined one when the motor speed has reached a predetermined value, i.e., if the motor current value is not less than 0.12 A at 1000 rpm, the control part 51 determines that the magnetic re-coupling of the impeller to the rotor has been achieved.

Figure 8:
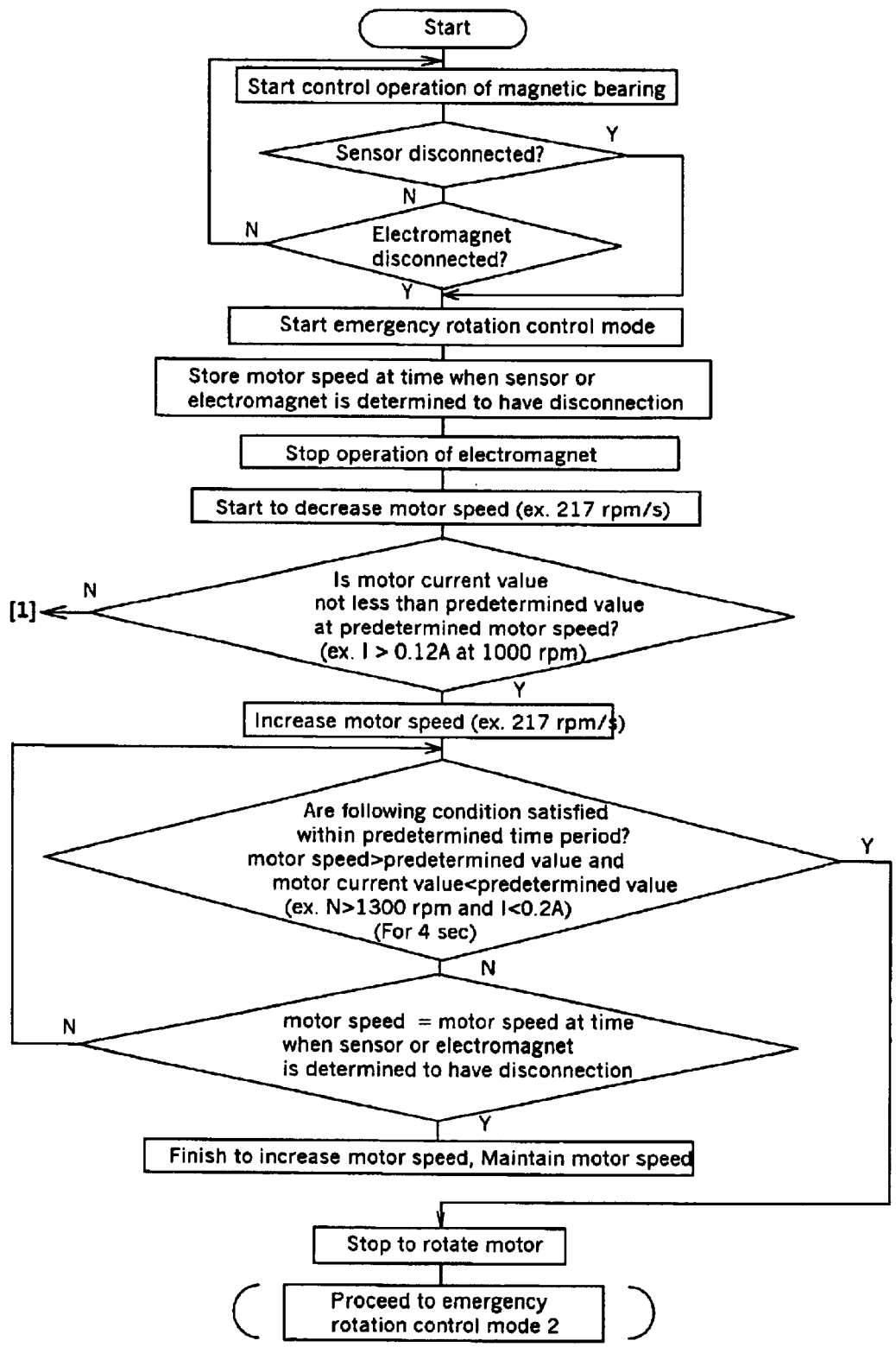
FIG. 8 is a flowchart for describing the operation of the centrifugal fluid pump apparatus of an embodiment of the present invention.

If the control part 51 determines that the magnetic re-coupling of the impeller to the rotor has been achieved, as shown in FIG. 8, the motor speed is increased at a predetermined increase ratio (first increase ratio), for example, in the range of 50 to 400 rpm/s, more specifically 217 rpm/s. Thereafter at a step of increasing the motor speed, the control part 51 determines whether the state in which the motor speed is more than the predetermined value (first predetermined value) and the motor current value is less than the predetermined value has continued for a predetermined period of time. More specifically, the control part 51 determines whether the state in which the motor speed is not less than 1300 rpm and the motor current value is less than 0.2 A has continued for several seconds (for example, not less than four seconds). That is, in the case where the motor speed has reached to the stored motor speed corresponding to the failure-detected time without detecting such a state at a re-coupling release determination step, the increase of the motor speed is stopped, and the motor speed is maintained. Thereby the shift to the non-contact rotation by means of the dynamic pressure bearing is completed. The timing chart of FIG. 7 shows the case in which the magnetic re-coupling has occurred at 1000 rpm as shown with a broken line.

When it is determined at the re-coupling release determination step that the magnetic re-coupling has been released, as shown in FIG. 8, the rotation of the motor is stopped. In the case where the centrifugal fluid pump apparatus has an emergency rotation control mode 2, the control part 51 goes thereto.

Figure 9:
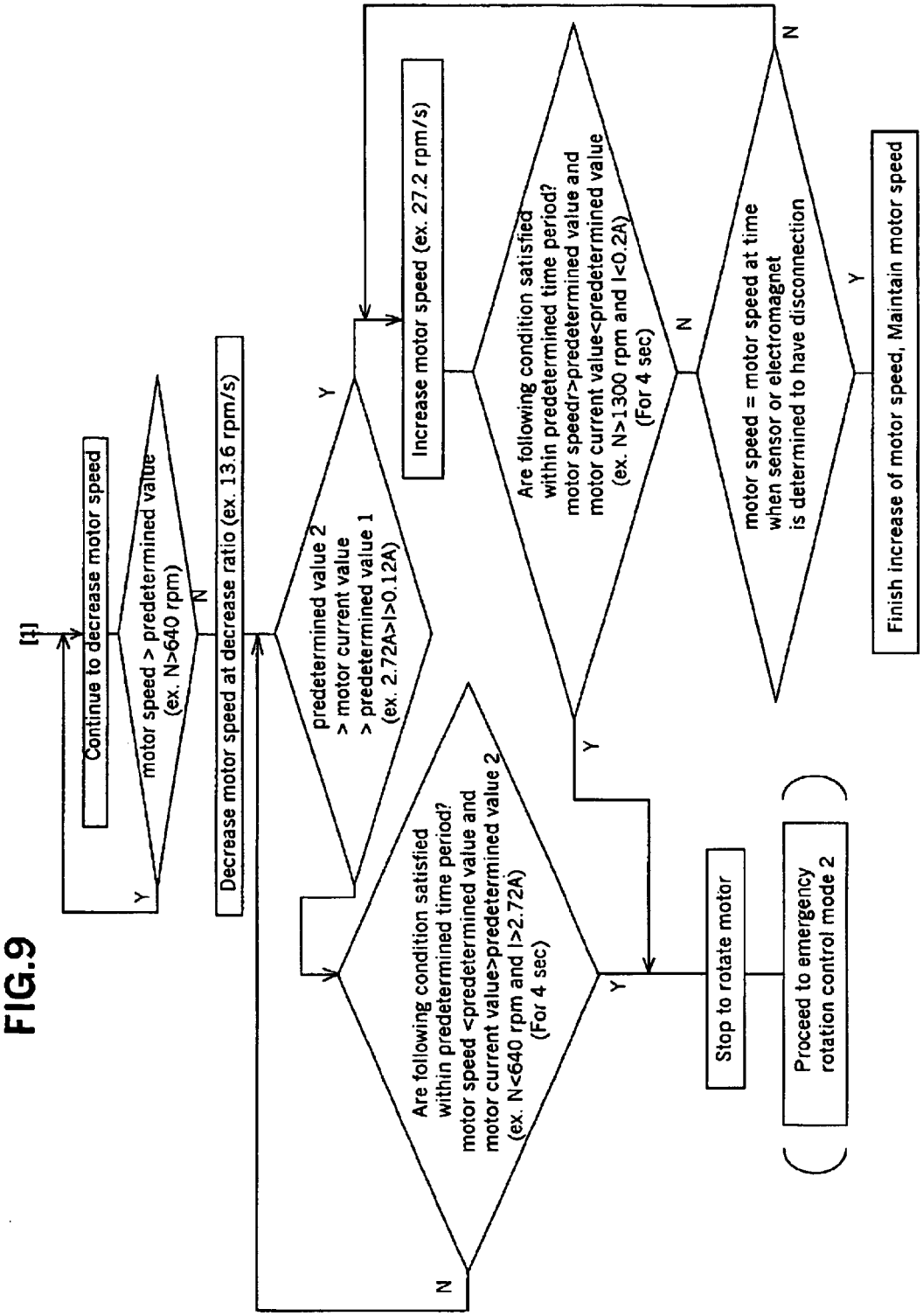
FIG. 9 is a flowchart for describing the operation of the centrifugal fluid pump apparatus of an embodiment of the present invention.

In the centrifugal fluid pump apparatus of the embodiment if at the impeller magnetic re-coupling execution step, the magnetic re-coupling condition is not satisfied when the motor speed is decreased at the first decrease ratio, the control part 51 goes to step [1] of FIG. 9 at which an operation of decreasing the motor speed at the first decrease ratio is continued until the motor speed reaches a predetermined value (second predetermined value), for example, 500–1000 rpm, more specifically, less than 640 rpm. If it is detected that the motor speed is less than the second predetermined value, the decrease of the motor speed is continued by altering the decrease ratio of the motor speed to a second decrease ratio less than the first decrease ratio. In the embodiment, favorably, the second decrease ratio is in the range of 5 to 100 rpm/s, more specifically, 13.6 rpm/s. This state is the impeller magnetic re-coupling execution step.

If it is detected at the impeller magnetic re-coupling execution step to be executed at the second decrease ratio that the motor current value falls within a predetermined range, the control part 51 determines that the magnetic re-coupling of the impeller to the rotor has been achieved. For example, if it is detected that the motor current value falls within the range of 0.12 to 2.72 A, the control part 51 determines that the magnetic re-coupling has been achieved.

If the control part 51 determines that the magnetic re-coupling of the impeller has been achieved, as shown in FIG. 9, the motor speed is increased at a predetermined increase ratio (second increase ratio smaller than first increase ratio), for example, in the range of 5 to 100 rpm/s, more specifically, 27.2 rpm/s. Thereafter at a step of increasing the motor speed, the control part 51 determines whether the state in which the motor speed is more than the predetermined value (first predetermined value) and the motor current value is less than the predetermined value has continued for a predetermined period of time. More specifically, the control part 51 determines whether the state in which the motor speed is not less than 1300 rpm and the motor current value is less than 0.2 A has continued for several seconds (for example, not less than four seconds). That is, in the case where the motor speed has reached the stored motor speed corresponding to the failure-detected time without detecting such a state at a re-coupling release determination step, the increase of the motor speed is stopped, and the motor speed is maintained. This case corresponds to the case of the timing chart shown with the solid line of FIG. 7.

At the impeller magnetic re-coupling execution step to be executed at the second decrease ratio the control part 51 determines whether the state in which the motor speed is less than the predetermined value (second predetermined value) and the motor current is more than a predetermined value (second predetermined value) has continued for a predetermined period of time. More specifically, the control part 51 determines whether the state in which the motor speed is less than 640 rpm and the motor current value is more than 2.72 A has continued for several seconds (for example, not less than four seconds). That is, it is determined whether the impeller 21 is in contact with the inner surface of the housing at the rotor side. The decrease of the motor speed is continued until the state in which the impeller 21 is in contact with the inner surface of the housing at the rotor side is detected. If it is determined that the impeller 21 is in contact with the inner surface of the housing at the rotor side and that the re-coupling has been released, the rotation of the motor is stopped, as shown in FIG. 9. In the case where the centrifugal fluid pump apparatus has the emergency rotation control mode 2, the control part 51 goes thereto.

Figure 10:
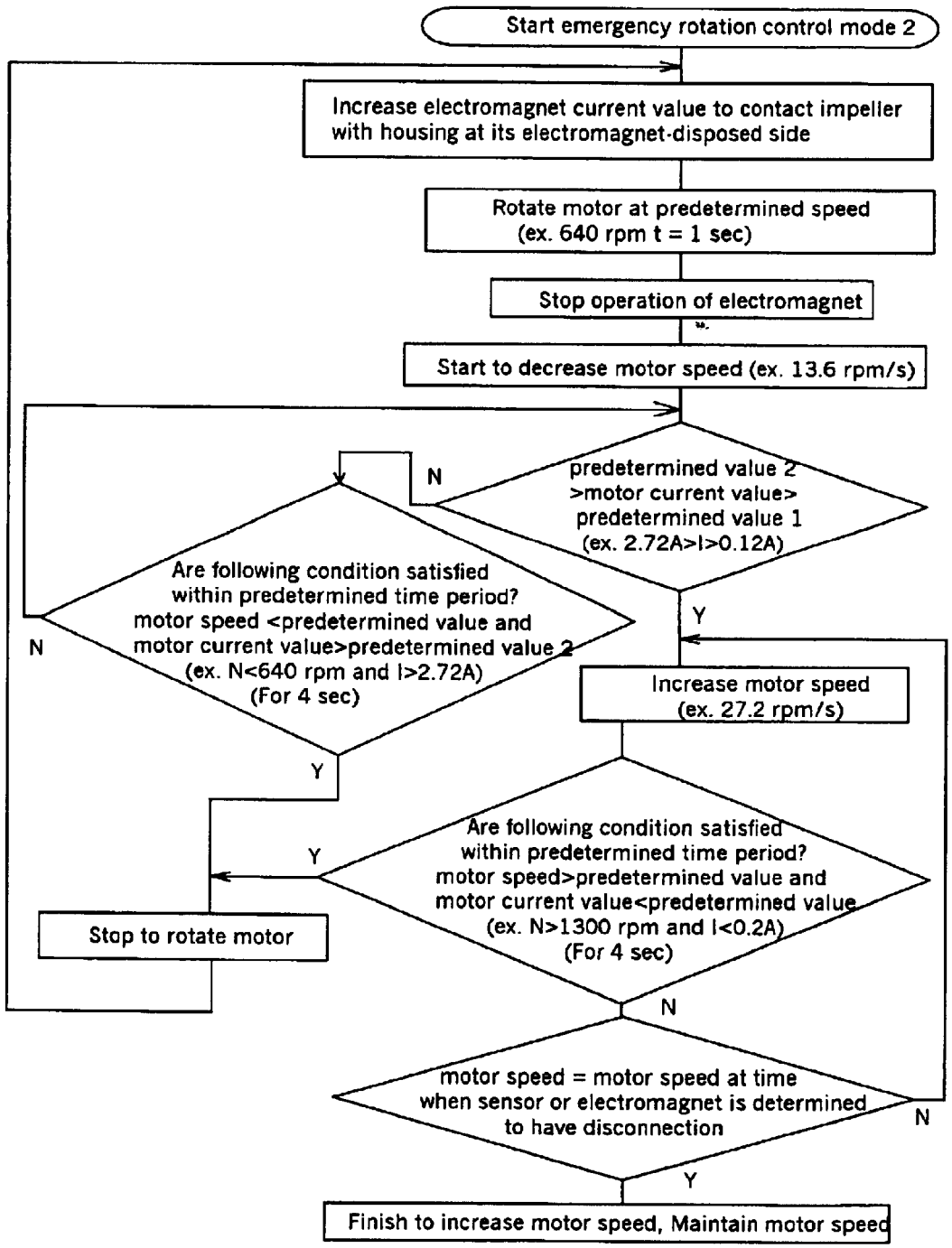
FIG. 10 is a flowchart for describing the operation of the centrifugal fluid pump apparatus of an embodiment of the present invention.

The emergency rotation control mode 2 shown in FIG. 10 is described below.

When the control part 51 goes to the emergency rotation control mode 2, as shown in FIG. 10, the electromagnet current value is increased to bring the impeller 21 into contact with the inner surface of the housing 20 at the electromagnet side. In other words, a step of forcibly bringing the impeller 21 into contact with the housing at the side of the electromagnet 41 is executed. If any one of the electromagnets fails, such a state can be generated by using remaining electromagnets. In this state, the motor is rotated at a predetermined motor speed, for example, in the range of 400 to 800 rpm, more specifically, 640 rpm. In other words, a step of rotating the motor is executed, with the impeller forcibly being brought into contact with the housing at the side of the electromagnet.

Thereafter the operation of the electromagnet is stopped. Then the motor speed is decreased at a predetermined decrease ratio (third decrease ratio smaller than first decrease ratio, for example, in the range of 5 to 100 rpm/s, more specifically, 13.6 rpm/s). This state is an impeller magnetic re-coupling execution step in the mode 2.

If it is detected at the impeller magnetic re-coupling execution step to be executed at the third decrease ratio that the motor current value falls within a predetermined range, the control part 51 determines that the magnetic re-coupling of the impeller to the rotor has been achieved. For example, if it is detected that the motor current falls within the range of 0.12 to 2.72 A, the control part 51 determines that the impeller magnetic re-coupling has been achieved.

If the control part 51 determines that the impeller magnetic re-coupling has been achieved, as shown in FIG. 10, the motor speed is increased at a predetermined increase ratio (second increase ratio smaller than first increase ratio), for example, in the range of 5 to 100 rpm/s, more specifically, 27.2 rpm/s. Thereafter at a step of increasing the motor speed, the control part 51 determines whether the state in which the motor speed is more than a predetermined value (first predetermined value) and the motor current value is less than a predetermined value has continued for a predetermined period of time. More specifically, the control part 51 determines whether the state in which the motor speed is not less than 1300 rpm and the motor current value is less than 0.2 A has continued for several seconds (for example, not less than four seconds). That is, in the case where the motor speed has reached a stored motor speed corresponding to a failure-detected time without detecting such a state at a re-coupling release determination step, the increase of the motor speed is stopped, and the motor speed is maintained.

At the impeller magnetic re-coupling execution step to be executed at the third decrease ratio, the control part 51 determines whether the state in which the motor speed is less than a predetermined value (second predetermined value) and the motor current is more than a predetermined value (second predetermined value) has continued for a predetermined period of time. More specifically, the control part 51 determines whether the state in which the motor speed is less than 640 rpm and the motor current value is more than 2.72 A has continued for several seconds (for example, not less than four seconds). That is, it is determined whether the impeller 21 is in contact with the inner surface of the housing at the rotor side. The decrease of the motor speed is continued until the state in which the impeller 21 is in contact with the inner surface of the housing at the rotor side is detected. If it is determined that the impeller 21 is in contact with the inner surface of the housing at the rotor side and that the re-coupling has been released, the rotation of the motor is stopped, as shown in FIG. 10. Then the mode 2 is executed from the first step. That is, at the impeller magnetic re-coupling execution step, until the rotation of the impeller is achieved by the support of the dynamic pressure bearing, the above-described operation is repeatedly executed.

Figure 11:
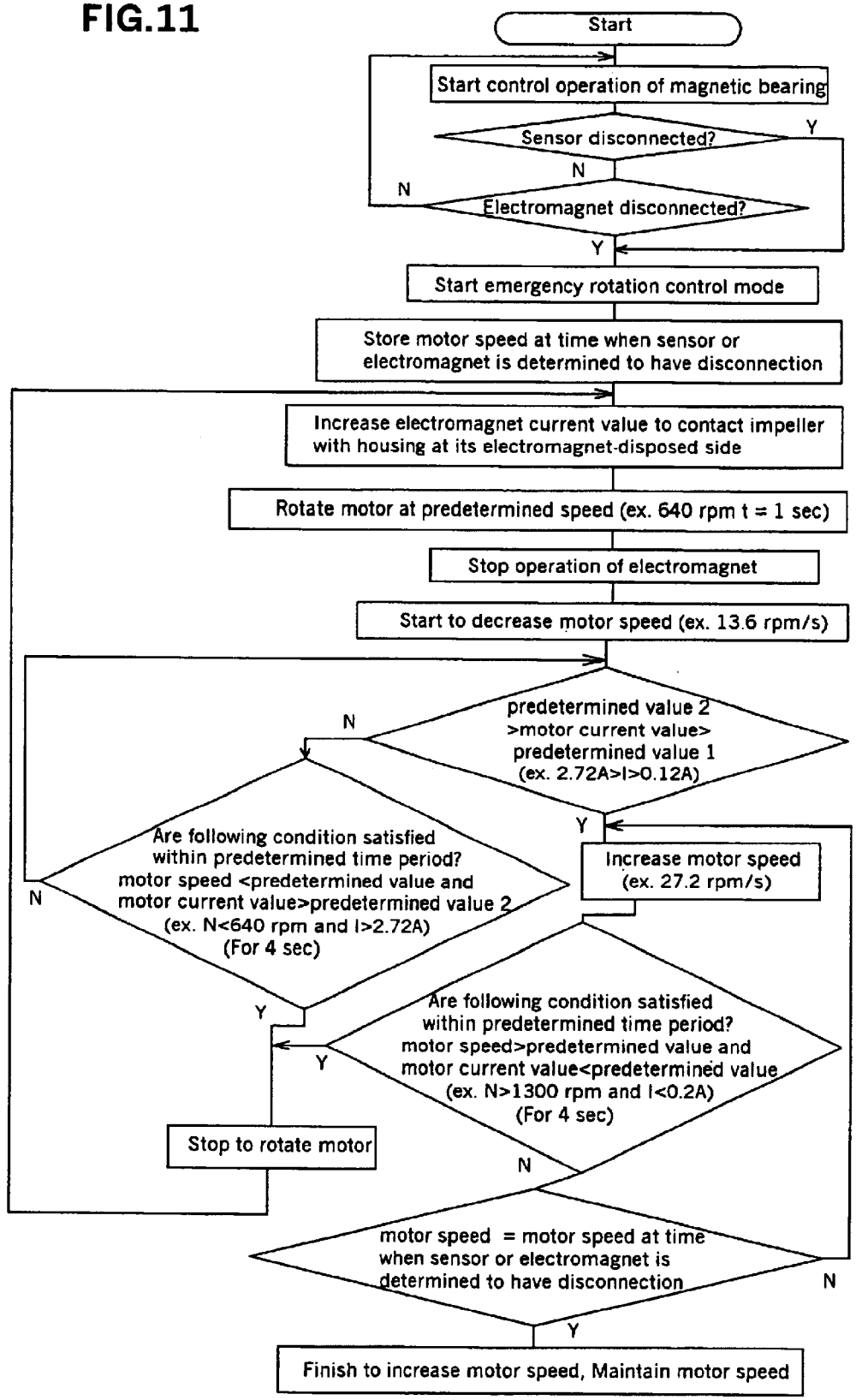
FIG. 11 is a flowchart for describing the operation of the centrifugal fluid pump apparatus of an embodiment of the present invention.

The emergency impeller rotation function of the centrifugal fluid pump apparatus may be performed as shown in FIG. 11.

A magnetic bearing pump rotates at not less than 1200 rpm and more specifically at 1450 rpm. If the control system of the magnetic bearing has a trouble (failure of magnetic bearing), as shown in the flowchart of FIG. 11, i.e., if the control part 51 determines that the sensor or the electromagnet has disconnection, an emergency rotation control mode starts to operate. The control part 51 stores the motor speed at the time when it is determined that the sensor or the electromagnet has disconnection.

Then as shown in FIG. 11, the electromagnet current value is increased to bring the impeller 21 into contact with the inner surface of the housing 20 at the side of the electromagnet 41. In other words, a step of forcibly bringing the impeller into contact with the housing at the side of the electromagnet 41 is executed. If any one of the electromagnets fails, such a state can be generated by using remaining electromagnets. In this state, the motor is rotated at a predetermined motor speed, for example, in the range of 400 to 800 rpm, more specifically, 640 rpm. In other words, a step of rotating the motor is executed, with the impeller forcibly being brought into contact with the housing at the side of the electromagnet.

Thereafter the operation of the electromagnet is stopped. Then the motor speed is decreased at a predetermined decrease ratio (for example, in the range of 5 to 100 rpm/s, more specifically, 13.6 rpm/s). This state is an impeller magnetic re-coupling execution step.

If it is detected at the impeller magnetic re-coupling execution step that the motor current value falls within a predetermined range, the control part 51 determines that the magnetic re-coupling of the impeller has been achieved. For example, if it is detected that the motor current value falls within the range of 0.12 to 2.72 A, the control part 51 determines that the magnetic re-coupling of the impeller has been achieved.

If the control part 51 determines that the impeller magnetic re-coupling has been achieved, as shown in FIG. 11, the motor speed is increased at a predetermined increase ratio, for example, in the range of 5 to 100 rpm/s, more specifically, 27.2 rpm/s. Thereafter at a step of increasing the motor speed, the control part 51 determines whether the state in which the motor speed is more than a predetermined value (first predetermined value) and the motor current value is less than a predetermined value has continued for a predetermined period of time. More specifically, the control part 51 determines whether the state in which the motor speed is not less than 1300 rpm and the motor current value is less than 0.2 A has continued for several seconds (for example, not less than four seconds). That is, in the case where the motor speed has reached the stored motor speed corresponding to the failure-detected time without detecting such a state at a re-coupling release determination step, the increase of the motor speed is stopped, and the motor speed is maintained.

At the impeller magnetic re-coupling execution step, the control part 51 determines whether the state in which the motor speed is less than a predetermined value (second predetermined value) and the motor current is more than a predetermined value (second predetermined value) has continued for a predetermined period of time. More specifically, the control part 51 determines whether the state in which the motor speed is less than 640 rpm and the motor current value is more than 2.72 A has continued for several seconds (for example, not less than four seconds). That is, it is determined that the impeller 21 is in contact with the inner surface of the housing at the rotor side. The decrease of the motor speed is continued until the state in which the impeller 21 is in contact with the inner surface of the housing at the rotor side is detected. If it is determined that the impeller 21 is in contact with the inner surface of the housing at the rotor side and that the re-coupling has been released, the rotation of the motor is stopped, as shown in FIG. 11. Then the control part 51 goes to a step of bringing the impeller 21 into contact with the inner surface of the housing at the electromagnet side by increasing the electromagnet current. That is, at the impeller magnetic re-coupling execution step, until the rotation of the impeller is achieved by means of the groove for hydrodynamic bearing, the above-described operation is repeatedly executed.

The centrifugal fluid pump apparatus of this invention includes the position sensor output monitoring function or the electromagnet current monitoring function; the motor current monitoring function; the failure detection function for determining a failure of the sensor by using said position sensor output monitoring function or a failure of the electromagnet by using said electromagnet current monitoring function; and the emergency impeller rotation function operating when the failure detection function detects that the sensor has a failure to rotate the impeller by utilizing the groove for hydrodynamic bearing without substantial contact between the impeller and the housing. The emergency impeller rotation function has the impeller magnetic re-coupling execution function of stopping the electromagnet from attracting the impeller thereto, when the failure is detected by the failure detection function and gradually decreasing the motor speed to thereby execute magnetic coupling between the impeller and the rotor; the magnetic re-coupling detection function of detecting magnetic re-coupling of the impeller by using a motor current monitored by the motor current monitoring function; and the motor speed control function by increasing the motor speed up to the predetermined value after the magnetic re-coupling detection function detects the magnetic re-coupling of the impeller.

Thereby in the case where the position sensor or the electromagnet which constitute the control system of the magnetic bearing have a trouble, it is possible to shift the rotation of the impeller that is made by the magnetic bearing to the rotation thereof that is made by utilizing the pressure generated by the groove for hydrodynamic bearing. Thus it is possible to maintain feeding of a liquid.

While the preferred form of the present invention has been described, it is to be understood that modifications will be apparent to those skilled in the art without departing from the spirit of the invention. The scope of the invention, therefore, is to be determined solely by the following claims.

What is claimed is:

1. A centrifugal fluid pump apparatus comprising a pump body in which an impeller rotates without contacting a housing; and control means for controlling said pump body, said pump body comprising:

said housing having a blood inlet port and a blood outlet port;

a centrifugal pump section including an impeller having a first magnetic material and a second magnetic material and rotating in said housing to feed a fluid by a centrifugal force generated during its rotation;

an impeller rotational torque generation section including a rotor having a magnet for attracting said first magnetic material of said impeller and a motor for rotating said rotor;

an impeller position control section having an electromagnet for attracting said second magnetic material of said impeller;

a position sensor for detecting a position of said impeller; and a groove for hydrodynamic bearing provided on an inner surface of said housing at a side of said rotor or on a surface of said impeller at a side of said rotor, said control means:

monitoring at least one of an output of the position sensor and a current of the electromagnet;

monitoring a motor current;

determining at least one of a failure of the sensor or a failure of the electromagnet by using said monitoring of at least one of the output of the position sensor and the current of the electromagnet; and operating in an emergency impeller rotation control mode upon detection of the failure of the sensor or the failure of the electromagnet to rotate said impeller by utilizing said groove for hydrodynamic bearing without substantial contact between said impeller and said housing, said control means:

stopping said electromagnet from attracting said impeller upon detection of said failure and gradually decreasing a motor speed to thereby execute magnetic coupling between said impeller and said rotor;

detecting magnetic re-coupling between said impeller and said rotor by using the motor current monitored by said control means; and increasing the motor speed up to a predetermined value after detection of said magnetic re-coupling.

2. A centrifugal fluid pump apparatus according to claim 1, wherein said control means comprises a position senor output monitoring part which monitors the output of the position sensor and an electromagnet current monitoring part which monitors the current of the electromagnet, and said control means determines the failure of the sensor and the failure of the electromagnet.

3. A centrifugal fluid pump apparatus according to claim 1, further comprising a sensor circuit for said sensor which generates an output having a predetermined value exceeding a normal level when said sensor has disconnection, and said control means determines whether said sensor has a failure, based on the output of said position sensor monitored by said control means.

4. A centrifugal fluid pump apparatus according to claim 1, further comprising an electromagnet circuit for said electromagnet which is not energized when said electromagnet has disconnection, and said control means determines that said electromagnet has a failure when said control means monitors that electric current is not applied to said electromagnet circuit.

5. A centrifugal fluid pump apparatus according to claim 1, wherein when said control means detects a failure, said control means allows said rotor to rotate, with the impeller in contact with a surface of said housing opposite to a rotor-disposed side by attracting said impeller to said electromagnet to a higher extent before stopping said electromagnet from attracting said impeller thereto.

6. A centrifugal fluid pump apparatus according to claim 1, wherein said control means determines that the impeller and the rotor have become uncoupled from one another while the motor is rotating, with the motor speed being controlled by said control means after said magnetic re-coupling is accomplished.

7. A centrifugal fluid pump apparatus according to claim 6, wherein said control means stops rotation of the motor when said control means detects that said magnetic re-coupling is released.

8. A centrifugal fluid pump apparatus according to claim 1, wherein said control means operates in a second emergency impeller rotation control mode when said control means determines that said magnetic re-coupling is not made, wherein said control means rotates said rotor, with said impeller in contact with a surface of the housing opposite to a rotor-disposed side by attracting said impeller to the electromagnet to a higher extent, stops said electromagnet from attracting said impeller thereto, and decreases the motor speed gradually to thereby execute magnetic coupling between said impeller and said rotor; and said control means increases the motor speed up to a predetermined value after detecting that magnetic re-coupling between said impeller and said rotor has been accomplished.

9. A centrifugal fluid pump apparatus according to claim 1, wherein said control means stores a motor speed at a time when said control means detects a failure or at a time in the neighborhood of said time when said control means detects the failure; and the control means increases the motor speed to the stored motor speed.

10. A centrifugal fluid pump apparatus according to claim 1, wherein said control means determines that magnetic re-coupling between said impeller and said rotor has been made, when a motor current value at a predetermined motor speed is more than a predetermined motor current value.

11. A centrifugal fluid pump apparatus according to claim 1, wherein said control means successively decreases a motor speed at a first decrease ratio to a predetermined motor speed, and successively decreases the motor speed at a second decrease ratio lower than said first decrease ratio, if said magnetic re-coupling between said impeller and said rotor is not detected during said decrease of the motor speed at the first decrease ratio.

12. A centrifugal fluid pump apparatus according to claim 11, wherein said control means determines that said impeller has been re-coupled to said rotor when a motor current value falls within a predetermined range during said decrease of the motor speed at the second decrease ratio.

13. A centrifugal fluid pump apparatus according to claim 6, wherein said control means operates in a second emergency impeller rotation control mode when said control means detects that said impeller has been magnetically uncoupled from said rotor; and wherein said control means rotates said rotor, with said impeller in contact with a surface of the housing opposite to a rotor-disposed side, by attracting said impeller to the electromagnet to a higher extent, stops said electromagnet from attracting said impeller thereto, and decreases a motor speed gradually to thereby execute magnetic coupling between said impeller and said rotor, and said control means increases the motor speed up to a predetermined value detecting that magnetic re-coupling between said impeller and said rotor has been accomplished.

14. A centrifugal fluid pump apparatus according to claim 1, wherein said control means comprises a position sensor output monitoring part which monitors the output of the position sensor.

15. A centrifugal fluid pump apparatus according to claim 1, wherein said control means comprises an electromagnet current monitoring part which monitors the current of the electromagnet.

16. A method of operating a centrifugal fluid pump apparatus, the centrifugal pump apparatus comprising an impeller rotatable within a housing to feed a fluid by centrifugal force generated during rotation of the impeller, the housing having a blood inlet port and a blood outlet port, the impeller having a first magnetic material and a second magnetic material, a rotor positioned in the housing and having a magnet for attracting said first magnetic material of said impeller, a motor for rotating said rotor, an electromagnet positioned in the housing for attracting said second magnetic material of said impeller, a position sensor for detecting a position of said impeller, and a groove for hydrodynamic bearing provided on an inner surface of said housing at a side of said rotor or on a surface of said impeller at a side of said rotor, the method comprising monitoring at least one of an output of the position sensor and a current of the electromagnet to determine at least one of a failure of the sensor or a failure of the electromagnet;

monitoring current of the motor;

rotating said impeller, upon detecting the failure of the sensor or the failure of the electromagnet, by utilizing said groove for hydrodynamic bearing without substantial contact between said impeller and said housing;

stopping said electromagnet from attracting said impeller upon detecting said failure, and gradually decreasing a motor speed to execute magnetic coupling between said impeller and said rotor;

detecting magnetic re-coupling between said impeller and said rotor by using the motor current; and increasing the motor speed up to a predetermined value after detecting the magnetic re-coupling between said impeller and said rotor.

17. A method of operating a centrifugal fluid pump apparatus according to claim 16, further comprising generating a sensor output having a predetermined value exceeding a normal level when said position sensor has been disconnected, and determining whether said sensor has a failure based on the monitored output of said position sensor.

18. A method of operating a centrifugal fluid pump apparatus according to claim 16, wherein the apparatus comprises an electromagnet circuit for said electromagnet which is not energized when said electromagnet has disconnection, the method further comprising determining that said electromagnet has a failure when it is determined that electric current is not applied to said electromagnet circuit.

19. A method of operating a centrifugal fluid pump apparatus according to claim 16, wherein, upon detecting a failure, said rotor is rotated with the impeller in contact with a surface of said housing opposite to a rotor-disposed side by attracting said impeller to said electromagnet to a higher extent before stopping said electromagnet from attracting said impeller thereto.

20. A method of operating a centrifugal fluid pump apparatus according to claim 16, further comprising determining that the impeller and the rotor have become uncoupled from one another while the motor is rotating, and controlling the motor speed after said magnetic re-coupling is accomplished.

* * * * *